(12) United States Patent
Rampona

(10) Patent No.: US 7,211,077 B1
(45) Date of Patent: May 1, 2007

(54) METHODS FOR REMOVING EPITHELIAL CELLS PRIOR TO PERFORMING CORNEAL ABLATION

(76) Inventor: Douglas M. Rampona, 1828 N. Alanton Dr., Virginia Beach, VA (US) 23454-1548

( * ) Notice: Subject to any disclaimer, the term of this patent is extended or adjusted under 35 U.S.C. 154(b) by 0 days.

(21) Appl. No.: 11/172,576

(22) Filed: Jun. 30, 2005

Related U.S. Application Data

(60) Provisional application No. 60/635,532, filed on Dec. 13, 2004.

(51) Int. Cl.
*A61B 18/20* (2006.01)

(52) U.S. Cl. ............................... 606/5; 606/4; 128/898

(58) Field of Classification Search ................ 606/4–6, 606/166; 128/898
See application file for complete search history.

(56) References Cited

U.S. PATENT DOCUMENTS

| | | | | |
|---|---|---|---|---|
| 5,312,330 | A | * | 5/1994 | Klopotek ................... 604/521 |
| 5,318,046 | A | * | 6/1994 | Rozakis ....................... 128/898 |
| 5,520,679 | A | * | 5/1996 | Lin .................................. 606/5 |
| 5,613,965 | A | * | 3/1997 | Muller .......................... 606/5 |
| 5,632,757 | A | * | 5/1997 | Arnott ........................ 606/166 |
| 5,964,748 | A | * | 10/1999 | Peyman ........................... 606/5 |
| 6,068,625 | A | * | 5/2000 | Clapham ......................... 606/4 |
| 6,126,668 | A | * | 10/2000 | Bair et al. .................. 606/166 |
| 6,203,538 | B1 | * | 3/2001 | Peyman ........................... 606/5 |
| 6,210,401 | B1 | * | 4/2001 | Lai .............................. 606/12 |
| 6,706,036 | B2 | * | 3/2004 | Lai .............................. 606/12 |
| 6,793,654 | B2 | * | 9/2004 | Lemberg ......................... 606/5 |

OTHER PUBLICATIONS

"Renewed Interest in Modified Transepithelial Laser Ablation," Ocular Surgery News, vol. 22, No. 14, Jul. 15, 2004.*
*Renewed Interest in Modified Transepithelial Laser Ablation*; Douglas M. Rampona; Ocular Surgery News; vol. 22, No. 14, Jul. 15, 2004.

\* cited by examiner

*Primary Examiner*—A. Farah
(74) *Attorney, Agent, or Firm*—Bowman Green Hampton & Kelly, PLLC

(57) ABSTRACT

Methods for removing certain of the cells of the epithelium prior to performing corneal ablation, comprising, ablating certain of the cells of the epithelium in an area above the cornea to form an initial, substantially circular refractive curve in the epithelium, wherein the initial refractive curve is formed above an area of the cornea that will be ablated during the corrective eye surgery, and ablating certain additional cells of the epithelium to translate the initial refractive curve downward to define a bed in the epithelium, wherein the certain additional cells of the epithelium are ablated until the Bowman's membrane is at least partially exposed.

15 Claims, 6 Drawing Sheets

METHODS FOR REMOVING EPITHELIAL CELLS PRIOR TO PERFORMING CORNEAL ABLATION

CROSS-REFERENCE TO RELATED APPLICATIONS

This nonprovisional patent application claims the benefit of U.S. Provisional Patent Application Ser. No. 60/635,532, filed Dec. 13, 2004, the entire disclosure of which is incorporated herein by reference.

BACKGROUND OF THE INVENTION

1. Field of the Invention

This invention relates generally to corrective eye surgery. In particular, the present invention relates to methods for using a laser to perform corrective eye surgery.

2. Description of Related Art

It is well known that the eye receives its refracting power from several curved surfaces, each of which is separated by media with different indices of refraction. The most significant refractive surfaces in the eye are the anterior and posterior cornea and the anterior and posterior crystalline lens.

In a normal eye, that does not have any refractive errors, an emmetropic eye, the range of corneal refracting power is between 39 and 48 diopters, the range of lenticular refracting power is between 15 and 24 diopters, and the distance from the posterior corneal surface to the retina is between 22 to 26 millimeters.

The cornea, which is the transparent dome that serves as the outer window of the eye, is the primary and most powerful structure focusing light entering the eye. The cornea occupies one-sixth of the outer layer of the forward portion of the eye and is comprised, for the most part, of connective tissue with a thin, protective layer of epithelium on the surface.

PRK (Photo Refractive Keratectomy), which was introduced in 1987, was the first laser treatment to correct vision. Since then, a myriad of other correction techniques have been marketed. Some techniques have disappeared, while others have advanced.

PRK has had a resurgence of popularity mainly among surgeons who have reviewed the overall safety, predictability, and outcome results of PRK versus other procedures. PRK is very stable and can be used on certain people that no other procedure would be advisable. It is also the procedure of choice for those approaching the 50-year mark.

PRK is a laser treatment done directly on the surface of the cornea, as opposed to creating a flap, as with Lasik (Laser-Assisted Stromal In-situ Keratomileusis). Lasik complications typically have to do with flap creation or the flap healing process. Those patients at about age 50 and older experience flap healing complications at a rate of about 11% with Lasik. The surface cells tend to grow under the flap creating vision difficulties. There are no predicting factors (except age) as to whom this may affect. This 11% may face a long and frustrating process.

SUMMARY OF THE INVENTION

The present invention relates generally to methods for performing corrective eye surgery. In particular, the present invention relates to methods for using certain laser ablation patterns to remove epithelial cells above an area of the cornea prior to performing surface laser corrective eye surgery.

For precise and accurate corneal ablation to be performed, it is necessary that all of the epithelial cells in the epithelial layer above the area of the cornea that will be ablated, the bed, be removed and a clear starting point created at the outset, before the corneal ablation portion of the corrective eye surgery is performed.

Accordingly, this invention provides methods for performing corrective eye surgery, which provide superior safety.

This invention separately provides methods for performing corrective eye surgery, which provide improved vision when compared with other methods of corrective eye surgery.

This invention separately provides methods for removal of the epithelial cells above the area of the cornea that will be ablated, such that a clear starting point is created for performing corrective eye surgery.

This invention separately provides methods for accurate removal of the epithelial cells.

These and other features and advantages of this invention are described in or are apparent from the following detailed description of the exemplary embodiments.

BRIEF DESCRIPTION OF THE DRAWINGS

The exemplary embodiments of this invention will be described in detail, with reference to the following figures, wherein like reference numerals refer to like parts throughout the several views, and wherein.

DETAILED DESCRIPTION OF AN EXEMPLARY EMBODIMENT

For simplicity and clarification, the design factors and operating principles of the methods for performing corrective eye surgery according to this invention are explained with reference to various exemplary embodiments of methods for performing corrective eye surgery according to this invention. The basic explanation of the design factors and operating principles of the methods for performing corrective eye surgery is applicable for the understanding, design, and operation of the methods for performing corrective eye surgery of this invention.

Additionally, for simplicity and clarification, the methods of this invention will be described using the term "ablate". It should be understood that, in various exemplary embodiments, the term "ablate", as used herein, denotes the removal of tissue or material by laser ablation or vaporization. However, it should be appreciated that the ablation, or substantial vaporization, can be accomplish by any known or later developed instrument or device that is capable of emitting highly amplified and coherent radiation of one or more discrete frequencies.

Figure 1:
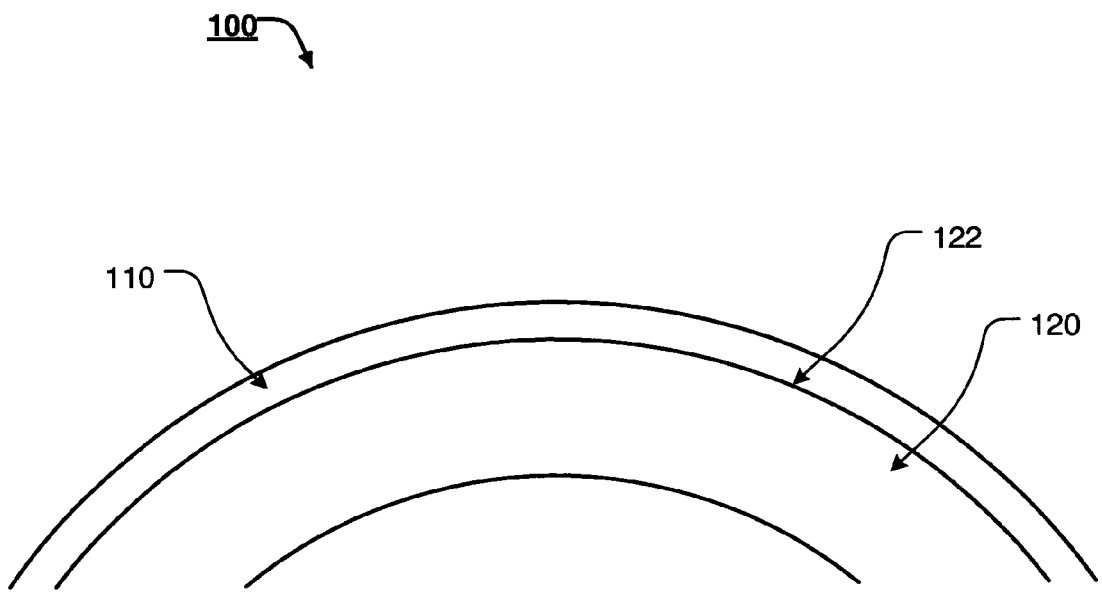
FIG. 1 shows a cross-sectional view of an exemplary eye.

FIG. 1 shows a cross-sectional view of an exemplary eye 100. As shown in FIG. 1, the eye 100 includes an epithelium 110 and a cornea 120. It should be appreciated that the cornea is comprised five layers, including the epithelium 110, the Bowman's membrane 122, the stroma (not shown), the Descemet's membrane (not shown), and the endothelium (not shown).

Figure 2:
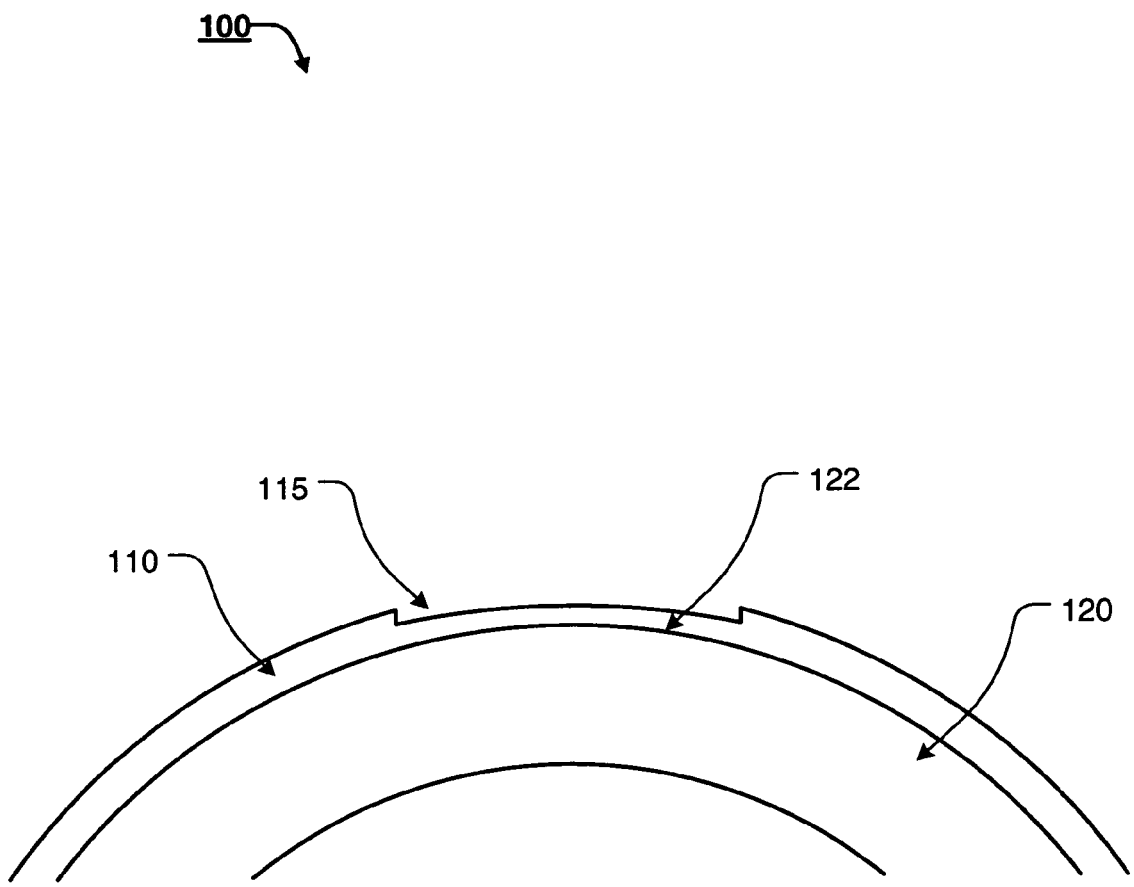
FIG. 2 shows a cross-sectional view of an exemplary eye wherein a portion of the epithelial layer has been removed according to a first exemplary embodiment of the methods for performing corrective eye surgery according to this invention.

FIG. 2 shows a cross-sectional view of an exemplary eye 100, wherein a portion of the epithelium 110 has been removed according to a first, illustrative, non-limiting exemplary embodiment of this invention. As shown in FIG. 2, certain of the cells of the epithelium 110 have been removed in an area 115 above the cornea 120. The area 115 is located above the area of the cornea 120 that will be ablated during the corrective eye surgery.

Because the central corneal epithelium is often ticker in the peripheral, a differential breakthrough pattern may be used. For example, early breakthrough may occur in the periphery with certain lasers and breakthrough patterns, while other lasers having different breakthrough patterns may provide for early breakthrough in the central corneal epithelium.

In various exemplary embodiments, a refractive curve, which substantially parallels the curvature of the Bowman's membrane, is chosen. In an illustrative, non-limiting embodiment of this invention, a −0.95 D to 40-μm refractive curve is used to remove the initial portion of the epithelium 110. In various exemplary embodiments, the refractive curve used to remove the epithelium 110 and form the surface of the bed 117 creates a slight flattening of the epithelium 110 as the epithelium 110 is removed.

The size or diameter of the area 115 is generally equivalent or larger than the diameter of the cornea 120 that will be reshaped during the corrective eye surgery and is determined based upon the extent of ablation that will be done to reshape the cornea 120. It should be appreciated that the considerations for determining the amount of reshaping that will be done to the cornea and the appropriate diameter of the area of the cornea 120 that will be ablated during the corrective eye surgery will be understood and apparent to those skilled in the art.

Figure 3:
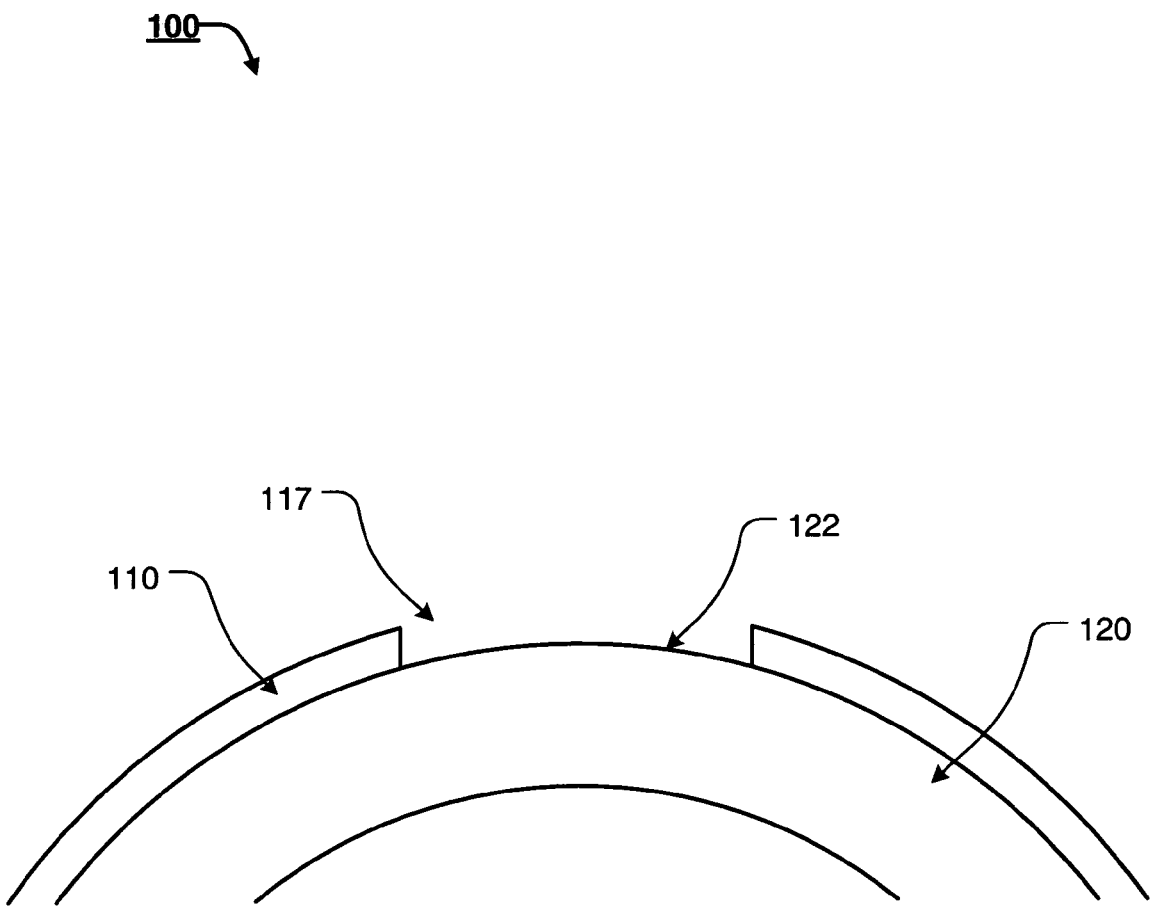
FIG. 3 shows a cross-sectional view of an exemplary eye wherein the epithelial layer has been removed according to a first exemplary embodiment of the methods for performing corrective eye surgery according to this invention.

FIG. 3 shows a cross-sectional view of an exemplary eye 100, wherein a portion of the epithelial layer 110 has been removed according to a first exemplary embodiment of the methods for performing corrective eye surgery according to this invention.

As shown in FIG. 3, once the initial refractive curve is created in the epithelium 110, the refractive curve is translated downward, ablating additional cells of the epithelium 110 and creating a bed 117.

The refractive curve is translated downward and additional cells of the epithelium 110, above the area of the cornea 120 that will be ablated, are removed until the Bowman's membrane 122 is exposed. When a refractive curve that substantially parallels the curvature of the Bowman's membrane is chosen, if breakthrough of the Bowman's membrane occurs, it generally does so in a uniform fashion.

The bed 117 is formed by continuing to remove cells from the epithelium 110 in the area 115. Therefore, the overall diameter of the bed 117 is generally equal to the diameter of the area 115.

In an illustrative, non-limiting embodiment of this invention, a −0.75 D refractive treatment combined with a 38-μm Phototherapeutic Keratectomy (PTK) for 21 seconds at 10 Hz is used to remove the epithelium 110 and form the surface of the bed 117. In other illustrative, non-limiting embodiments of this invention, a −0.85 D refractive treatment combined with a 40-μm PTK for 21 seconds at 10 Hz is used to remove the epithelium 110 and form the surface of the bed 117.

In various exemplary embodiments of this invention, a 44-μm PTK mode is used and breakthrough of the epithelium 110 may be observed by slowing the repetition rate, dimming elimination, and optionally observing the disappearance of fluorescence in the appearance and a glistening Bowman's membrane. Generally, observation of breakthrough is not required.

For situations where there appears to be incomplete removal on the epithelium 110 by the laser (i.e., in cases of anterior basement membrane syndrome where there appears to be reduplicated, thickened epithelium 110), a brush or other technique may be used to completely remove the cells of the epithelium 110 from the bed 117. Typically, a few seconds of brushing are required to remove recalcitrant residual cells. The size of the bed 117 is not expanded by this treatment and the rate of the healing for the patient is generally not affected.

Once the appropriate portion of the epithelium 110 has been removed, debris may optionally be cleared from the surface of the cornea 120. In various exemplary embodiments, this may be done by making one pass with a Paton spatula or other similar device to clear any debris. Then, a dry Weck-Cel or other similar device may be used to wipe the surface of the cornea 120. Next, a thin film of balanced salt solution may be applied to the exposed surface of the cornea 120.

Next, the corneal ablation portion of the corrective eye surgery is performed.

Figure 4:
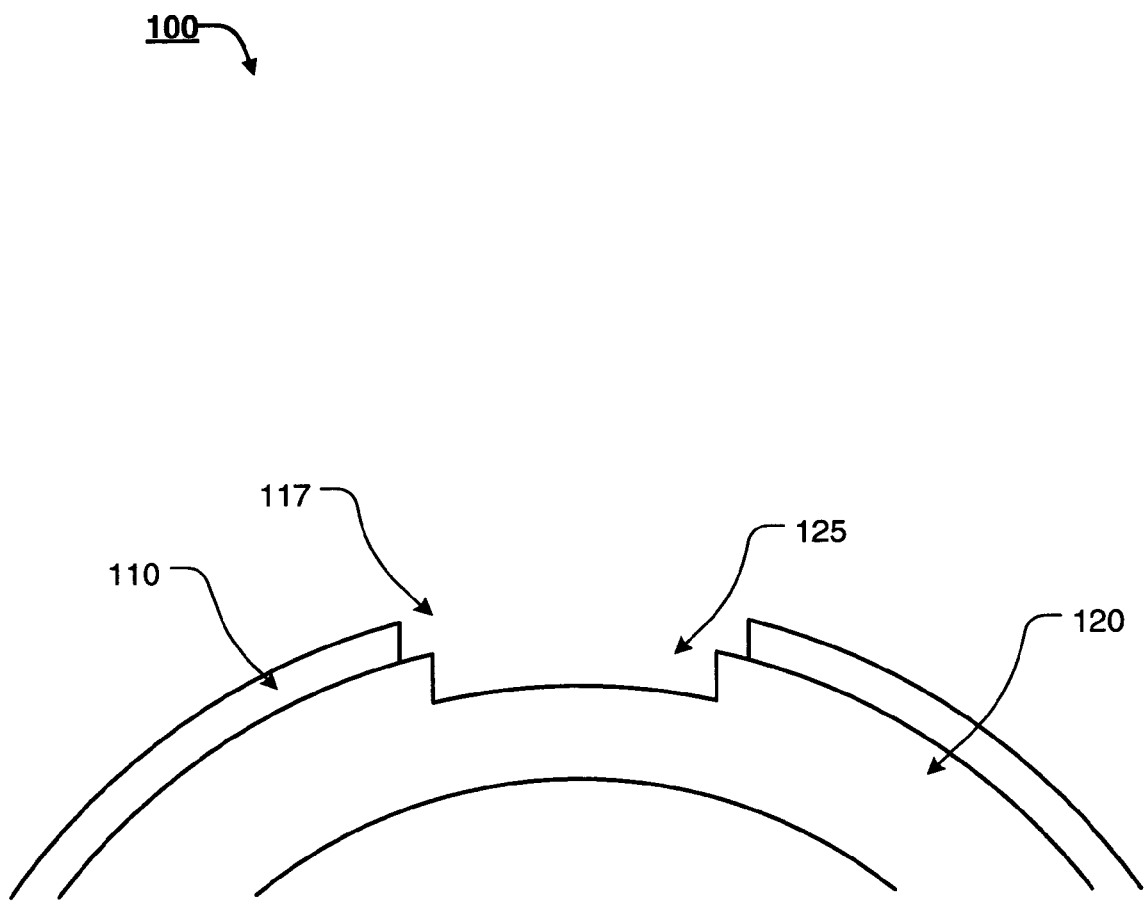
FIG. 4 shows a cross-sectional view of an exemplary eye wherein a portion of the cornea has been removed according to a first exemplary embodiment of the methods for performing corrective eye surgery according to this invention.

FIG. 4 shows a cross-sectional view of an exemplary eye 100, wherein the corneal ablation has been performed and a portion of the cornea 120 has been removed according to a first, illustrative, non-limiting exemplary embodiment of this invention. As shown in FIG. 4, a refractive curve 125 has been created by ablating at least a portion of the cornea 120.

It should be appreciated that, based on the amount of vision correction required by the patient, the degree of curvature and/or depth of ablation may be varied to provide an appropriate amount of vision correction.

Figure 5:
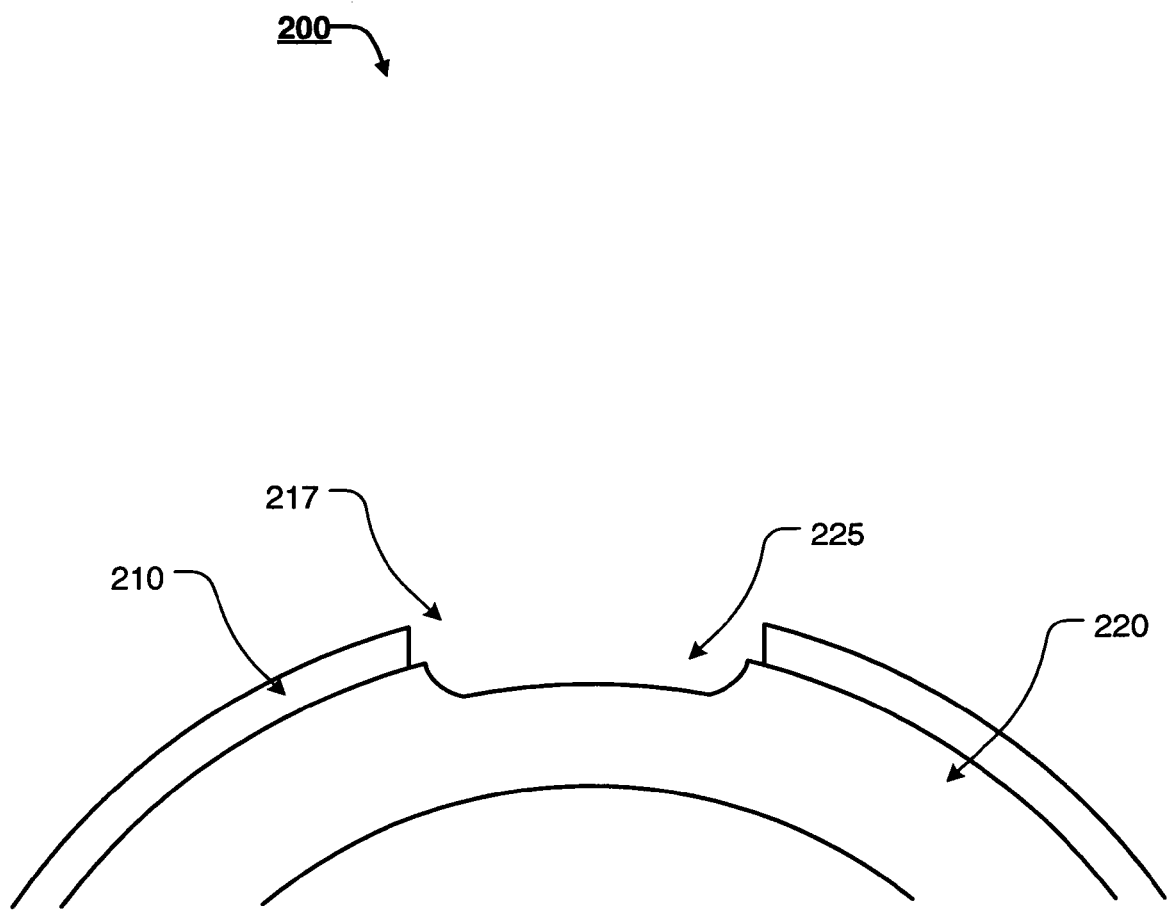
FIG. 5 shows a cross-sectional view of an exemplary eye wherein a portion of the cornea has been removed according to a second exemplary embodiment of the methods for performing corrective eye surgery according to this invention.

FIG. 5 shows a cross-sectional view of an exemplary eye 200, wherein a portion of the cornea has been removed according to a second, illustrative, non-limiting exemplary embodiment of this invention. As shown in FIG. 5, the cells of the epithelium 210, above the area of the cornea 220 that will be ablated, have been removed to form a bed 217, such that the Bowman's membrane 222 (not shown) is exposed.

Next, a refractive curve 225 has been created by ablating at least a portion of the cornea 220. As further shown in FIG.

5, the refractive curve 225 includes curved sidewalls, as opposed to the relatively angular walls depicted above, as shown in FIG. 4.

It should be appreciated that, based on the amount of vision correction required by the patient, the degree of curvature, side wall curvature, and/or depth of ablation may be varied to provide an appropriate amount of vision correction.

Figure 6:
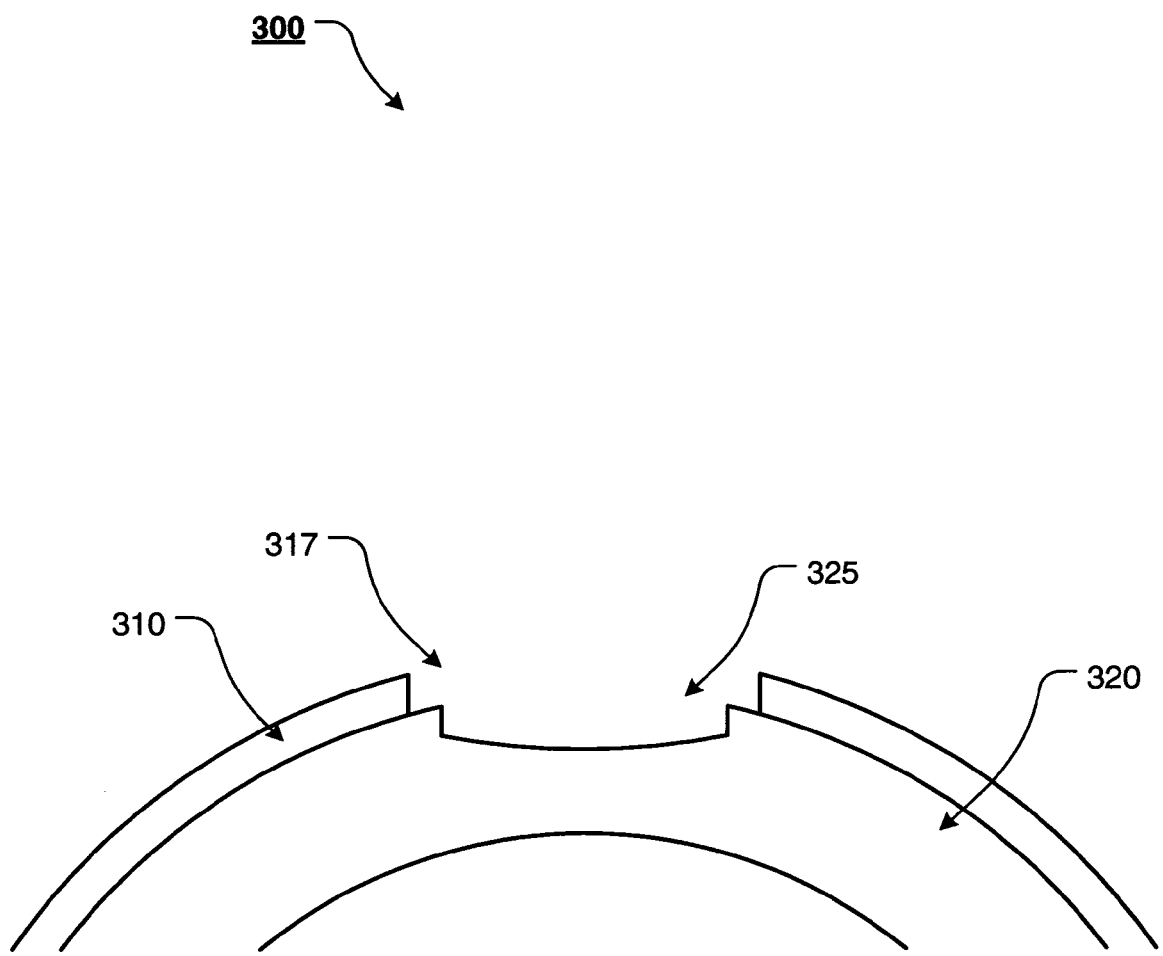
FIG. 6 shows a cross-sectional view of an exemplary eye wherein a portion of the cornea has been removed according to a third exemplary embodiment of the methods for performing corrective eye surgery according to this invention.

FIG. 6 shows a cross-sectional view of an exemplary eye 300, wherein the cells of the epithelium 310, above the area of the cornea 320 that will be ablated, have been removed to form a bed 317, such that the Bowman's membrane 322 (not shown) is exposed.

Next, a portion of the cornea 320 has been removed according to a third, illustrative, non-limiting exemplary embodiment of this invention. As shown in FIG. 6, a relatively concave curve 325 has been created by ablating at least a portion of the cornea 320.

It should be appreciated that, based on the amount of vision correction required by the patient, the degree of curvature, side wall curvature, and/or depth of ablation may be varied to provide an appropriate amount of vision correction.

Additionally, although the concave curve 325 is illustrated as including relatively angular walls, the concave curve may be formed having curved sidewalls, as opposed to the relatively angular walls.

While this invention has been described in conjunction with the exemplary embodiments outlined above, it is evident that many alternatives, modifications, and variations will be apparent to those skilled in the art. Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A method for removing certain of the cells of the epithelial layer of the cornea prior to performing corneal ablation, comprising:
    laser ablating certain of the epithelial cells in the epithelial layer of the cornea to form an initial refractive curve in the epithelial layer of the cornea, wherein the initial refractive curve is formed above an area of the cornea that will be ablated during the corrective eye surgery, and wherein a curvature of the refractive curve is approximately −0.75 D to −0.95 D; and
    laser ablating certain additional epithelial cells in the epithelial layer of the cornea to translate the initial refractive curve downward to define a bed in the epithelial layer of the cornea, wherein the certain additional epithelial cells in the epithelial layer of the cornea are laser ablated until the Bowman's membrane is at least partially exposed.

2. The method of claim 1, wherein a curvature of the refractive curve substantially parallels the curvature of the Bowman's membrane.

3. The method of claim 1, wherein a curvature of the refractive curve is approximately −0.75 D to −0.85 D.

4. The method of claim 1, wherein a diameter of the bed is approximately equivalent to the diameter of the area of the cornea that will be ablated during the corrective eye surgery.

5. The method of claim 1, wherein a diameter of the bed is larger than the diameter of the area of the cornea that will be ablated during the corrective eye surgery.

6. The method of claim 1, wherein certain additional cells of the epithelial layer of the cornea are ablated until the Bowman's membrane is completely exposed.

7. The method of claim 1, wherein a diameter of the bed at a surface of the bed is smaller than a diameter of the initial refractive curve.

8. The method of claim 1, wherein a diameter of the bed at a surface of the bed is equal to a diameter of the initial refractive curve.

9. The method of claim 1, further including the step of removing, via a brush, any epithelial cells that remain above the area of the cornea that will be ablated during the corrective eye surgery.

10. The method of claim 1, wherein a perimeter of the initial refractive curve is substantially circular.

11. The method of claim 1, wherein laser ablating certain of the epithelial cells in the epithelial layer of the cornea comprises substantially vaporizing certain of the epithelial cells in the epithelial layer of the cornea.

12. A method for removing certain of the cells of the epithelial layer of the cornea prior to performing corneal reshaping, comprising:
    substantially vaporizing certain of the cells of the epithelial layer of the cornea to define a bed, wherein the bed is formed above an area of the cornea that will be reshaped during the corrective eye surgery, wherein a curvature of the bed is approximately −0.75 D to −0.95 D, and wherein the certain cells of the epithelial layer of the cornea are substantially vaporized until the Bowman's membrane is at least partially exposed.

13. A method for preparing an eye for corneal ablation, comprising:
    laser ablating certain of the cells of the epithelial layer of the cornea to form an initial, substantially circular refractive curve in the epithelial layer of the cornea, wherein the initial refractive curve is formed above an area of the cornea that will be ablated during the corrective eye surgery, and wherein a curvature of the refractive curve is approximately −0.75 D to −0.95 D; and
    laser ablating certain additional cells of the epithelial layer of the cornea to translate the initial refractive curve downward to define a bed in the epithelial layer of the cornea, wherein the certain additional cells of the epithelial layer of the cornea are laser ablated until the Bowman's membrane is at least partially exposed.

14. The method of claim 12, wherein certain of the cells of the epithelial layer of the cornea are substantially vaporized by laser ablation.

15. The method of claim 13, wherein laser ablating certain of the epithelial cells in the epithelial layer of the cornea comprises substantially vaporizing certain of the epithelial cells in the epithelial layer of the cornea.

* * * * *